US009625250B2

(12) United States Patent
Lim et al.

(10) Patent No.: US 9,625,250 B2
(45) Date of Patent: Apr. 18, 2017

(54) APPARATUS AND METHOD OF GENERATING TOMOGRAPHIC IMAGE

(71) Applicants: Samsung Electronics Co., Ltd., Suwon-si (KR); Korea University Research and Business Foundation, Seoul (KR)

(72) Inventors: Jae-guyn Lim, Seongnam-si (KR); Beop-min Kim, Seoul (KR); Won-zoo Chung, Seoul (KR); Hyun-woo Jeong, Seoul (KR); Seong-deok Lee, Seongnam-si (KR); Woo-young Jang, Seongnam-si (KR)

(73) Assignees: Samsung Electronics Co., Ltd., Suwon-si (KR); Korea University Research and Business Foundation, Seoul (KR)

(*) Notice: Subject to any disclaimer, the term of this patent is extended or adjusted under 35 U.S.C. 154(b) by 817 days.

(21) Appl. No.: 13/871,456

(22) Filed: Apr. 26, 2013

(65) Prior Publication Data

US 2013/0289938 A1 Oct. 31, 2013

(30) Foreign Application Priority Data

Apr. 27, 2012 (KR) ........................ 10-2012-0044669

(51) Int. Cl.
  *H01J 3/14* (2006.01)
  *G01B 9/02* (2006.01)
  *A61B 5/00* (2006.01)

(52) U.S. Cl.
  CPC ....... *G01B 9/02091* (2013.01); *G01B 9/0201* (2013.01); *G01B 9/02083* (2013.01); *A61B 5/0066* (2013.01)

(58) Field of Classification Search
  USPC ................................ 250/216, 559.4, 363.04
  See application file for complete search history.

(56) References Cited

U.S. PATENT DOCUMENTS 5,994,690 A * 11/1999 Kulkarni .............. A61B 5/7257
  250/216
2007/0236699 A1  10/2007 Chou et al.
  (Continued)

FOREIGN PATENT DOCUMENTS

JP          4389032 B2   12/2009
WO      WO 02/04925 A1   1/2002

OTHER PUBLICATIONS

B. Baumann et al., "Full range complex spectral domain optical coherence tomography without additional phase shifters," *Optics Express*, vol. 15, No. 20, Oct. 1, 2007, pp. 13375-13387.

(Continued)

*Primary Examiner* — Lam Nguyen
(74) *Attorney, Agent, or Firm* — NSIP Law

(57) ABSTRACT

A method of generating a tomographic image includes detecting an interference signal containing cross-sectional information of a target object as raw data of the target object, the raw data being phase-modulated in a first direction with respect to a cross section of the target object; demodulating the raw data by adjusting at least one parameter of a filter function defining filtering using a fixed window size; and generating a tomographic image of the target object by performing signal processing on the demodulated raw data.

20 Claims, 7 Drawing Sheets

(56) References Cited

U.S. PATENT DOCUMENTS

2011/0170111 A1 7/2011 Rolland et al.
2011/0228221 A1 9/2011 Hanebuchi et al.

OTHER PUBLICATIONS

Y. Yasuno et al., "Simultaneous *B—M*-mode scanning method for real-time full-range Fourier domain optical coherence tomography," *Applied Optics*, vol. 45, No. 8, Mar. 10, 2006, pp. 1861-1865.
R. Wang et al.,"In vivo full range complex Fourier domain optical coherence tomography," *Applied Physics Letters*, vol. 90, No. 5, Jan. 29, 2007, pp. 054103-1 to 054103-3.
C.-T. Wu et al., "Method for suppressing the mirror image in Fourier-domain optical coherence tomography," *Optics Letters*, vol. 36, No. 15, Aug. 1, 2011, pp. 2889-2891.
H.-W. Jeong et al., "Complex artifact suppression using vestigial sideband filter in Fourier-domain optical coherence tomography," *Optics Letters*, vol. 37, No. 23, Dec. 1, 2012, pp. 4859-4861.
Extended European Search Report issued on Oct. 17, 2013, in counterpart European Application No. 13165549.0 (10 pages, in English).

\* cited by examiner

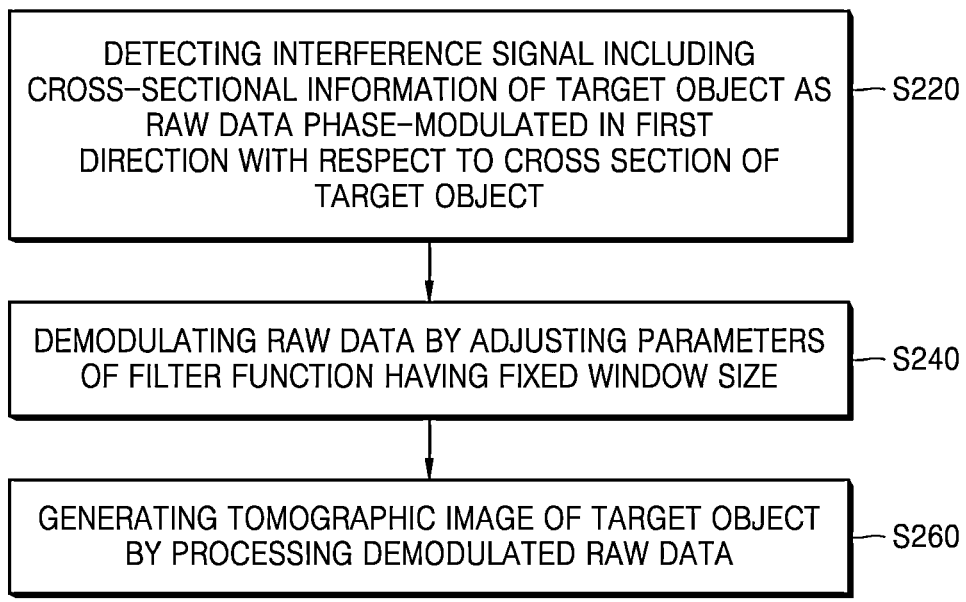
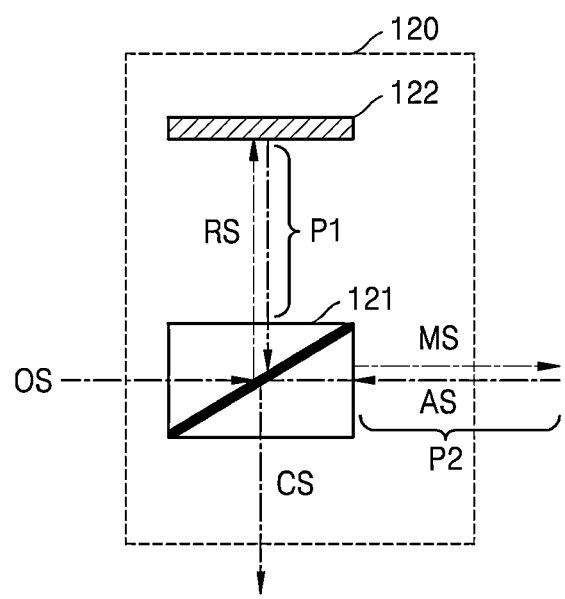

Folded
Part
AFTERIMAGE

Multiplication # = 4

Multiplication # = 16

APPARATUS AND METHOD OF GENERATING TOMOGRAPHIC IMAGE

CROSS-REFERENCE TO RELATED APPLICATIONS

This application claims the benefit of Korean Patent Application No. 10-2012-0044669 filed on Apr. 27, 2012, in the Korean Intellectual Property Office, the disclosure of which is incorporated herein by reference in its entirety.

BACKGROUND

1. Field

This application relates to apparatuses and methods of generating an accurate tomographic image of a target object without increasing the complexity of calculation that is required to generate the tomographic image.

2. Description of Related Art

Tomography is a technique of acquiring tomographic images of a target object using penetrating waves. Such tomography is used in various fields. Accordingly, requirements for generation of high quality tomographic images are also increasing. In particular, in the medical field directly related to human life, a technology for accurately generating tomographic images by using limited resources is emerging as an important issue.

SUMMARY

In one general aspect, a method of generating a tomographic image includes detecting an interference signal including cross-sectional information of a target object as raw data of the target object, the raw data being phase-modulated in a first direction with respect to a cross section of the target object; demodulating the raw data by adjusting at least one parameter of a filter function defining filtering within a fixed window size; and generating a tomographic image of the target object by performing signal processing on the demodulated raw data.

The at least one parameter may be a duration or a roll-off of the filter function.

The demodulating of the raw data may include adjusting a flatness of a waveform of the raw data by adjusting the at least one parameter.

The demodulating of the raw data may include performing an operation of multiplying each of first units of the raw data by the filter function defining the filtering a number of times corresponding to the fixed window size.

Each of the first units may be a row unit of the raw data.

The filter function may be a vestigial sideband filter (VSB) filter function.

The method may further include setting a window size of the VSB filter function as the fixed window size before demodulating the raw data.

The generating of the tomographic image of the target object may include performing signal processing on the demodulated raw data in a second direction perpendicular to the first direction.

The demodulated raw data may be in a wavelength domain; and the generating of the tomographic image of the target object may include converting the demodulated raw data in the wavelength domain into depth information about the target object.

The method of generating a tomographic image may be an optical coherent tomography (OCT) method.

In another general aspect, a non-transitory computer-readable storage medium stores a program for controlling a computer to perform the method described above.

In another general aspect, an apparatus for generating a tomographic image includes a light generation unit configured to generate an optical signal; an interferometer configured to split the optical signal into a measurement signal and a reference signal, and apply the measurement signal to a target object; a detector configured to detect an interference signal generated by interference between the reference signal and a response signal received from the target object in response to the application of the measurement signal as raw data of the target object, the raw data being phase-modulated in a first direction with respect to a cross section of the target object; and an image processing device configured to generate a tomographic image from the raw data; wherein the image processing device includes a fixed window filtering unit configured to demodulate the raw data by filtering the raw data using a fixed window size; and an image generating unit configured to generate the tomographic image of the target object by performing signal processing on the demodulated raw data.

The interference signal may be in a frequency domain; and the fixed window filtering unit may be further configured to set a shape of a waveform of the interference signal in the frequency domain by adjusting at least one parameter of a filter function defining the filtering.

The at least one parameter may be a duration or a roll-off of a filter function defining the filtering.

The fixed window filtering unit may include a vestigial sideband filter (VSB).

The fixed window filtering unit may be further configured to set a window size of the VSB as the fixed window size before demodulating the raw data.

The fixed window filtering unit may be further configured to perform an operation of multiplying the raw data by a filter function defining the filtering a number of times corresponding to the fixed window size.

The interference signal may include cross-sectional information of the target object as the raw data of the target object; and the fixed window filtering unit may be further configured to demodulate the raw data in first units corresponding to the first direction from the cross-sectional information of the target object.

The demodulated raw data may be in a wavelength domain; and the image generating unit may be further configured to perform the signal processing on the demodulated raw data in a second direction perpendicular to the first direction; and perform the signal processing by converting the demodulated raw data in the wavelength domain into depth information about the target object.

The apparatus for generating the tomographic image may be an optical coherent tomography (OCT) apparatus.

Other features and aspects will be apparent from the following detailed description, the drawings, and the claims.

BRIEF DESCRIPTION OF THE DRAWINGS

FIG. 2 is a flowchart illustrating an example of a method of generating a tomographic image.

FIG. 3 is a diagram illustrating a detailed example of an interferometer of FIG. 1;

DETAILED DESCRIPTION

Figure 1:
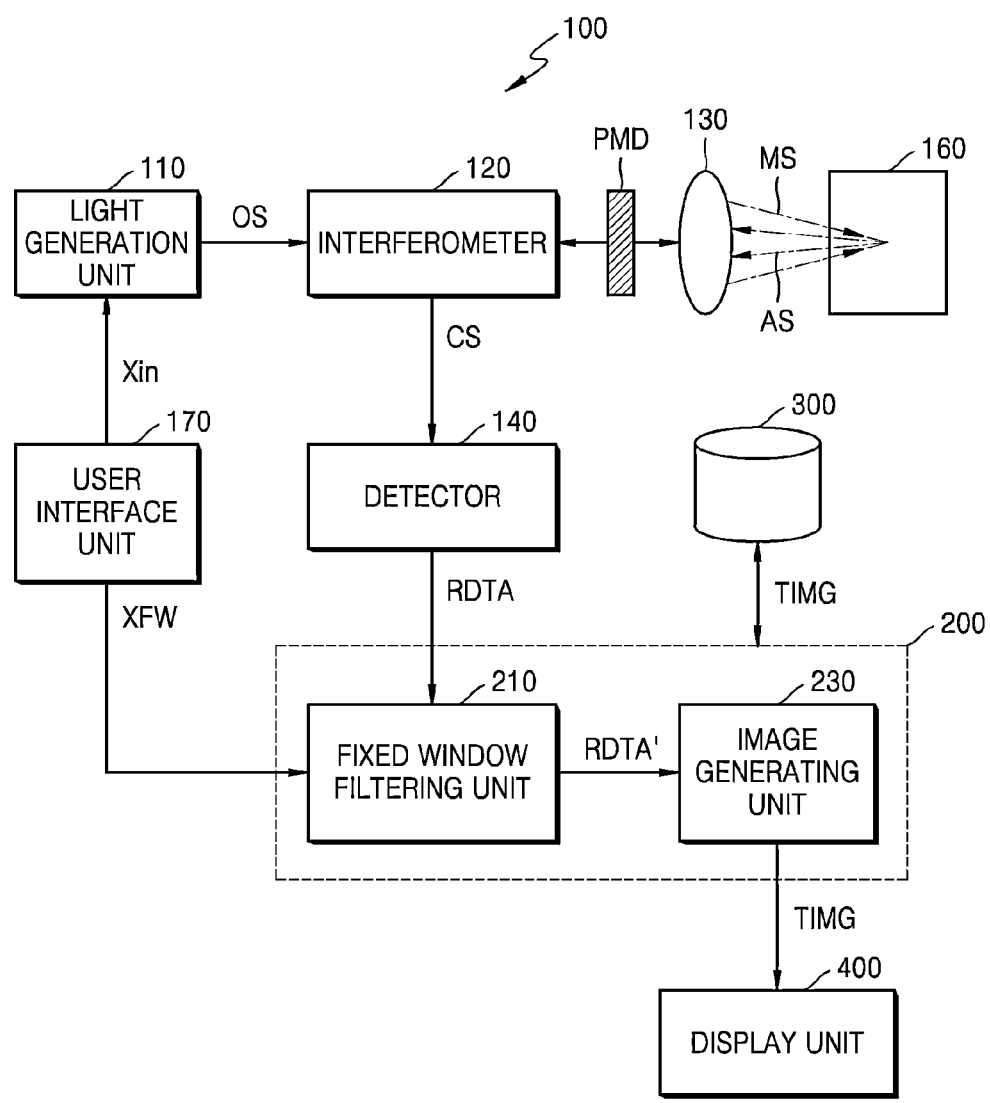
FIG. 1 is a block diagram illustrating an example of an apparatus for generating a tomographic image.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a block diagram illustrating an example of an apparatus 100 for generating a tomographic image, and FIG. 2 is a flowchart illustrating an example of a method of generating a tomographic image.

Referring to FIGS. 1 and 2, the apparatus 100 for generating a tomographic image (hereinafter referred to as a "tomographic image generating apparatus") may be an optical coherence tomography (OCT) apparatus. In this case, the tomographic image generating apparatus 100 includes a light generation unit 110, an interferometer 120, a detector 140, and an image processing device 200. The method of generating a tomographic image includes detecting an interference signal CS including cross-sectional information of a target object 160 as raw data RDTA phase-modulated in a first direction with respect to a cross section of the target object 160 (operation S220), demodulating the raw data RDTA by adjusting parameters of a filter function having a fixed window size (operation S240), and generating a tomographic image TIMG of the target object 160 by processing a result obtained by demodulating the interference signal CS (operation S260).

The detecting (operation S220) of the interference signal CS may be performed by operations of the light generation unit 110, the interferometer 120, a phase modulator PMD, and the detector 140. The light generation unit 110 generates an optical signal OS. For example, the light generation unit 110 may emit the optical signal OS in response to an interface signal Xin corresponding to an input from a user interface unit 170. In general, the user interface unit 170 may be an input device such as a keyboard, a mouse, or other input device. Alternatively, the user interface unit 170 may include a graphical user interface (GUI) that is displayed on a display unit 400. An event generated in the user interface unit 170 may be generated as the interface signal Xin. The event generated in the user interface unit 170 may be, for example, a keyup or keydown in the case where the user interface unit 170 is the keyboard, a click in the case where the user interface is the mouse, or a touch in the case where the user interface 170 is the GUI.

Examples of the optical signal OS generated from the light generation unit 110 may include a superluminescent diode (SLD) signal, or an edge-emitting light emitting diode (ELED) signal, or any other kind of optical signal. The optical signal OS generated from the light generation unit 110 is transmitted to the interferometer 120. The optical signal OS may be transmitted to the interferometer 120 through free space or through a transmission medium. The transmission medium may be, for example, an optical fiber.

FIG. 3 is a diagram illustrating a more detailed example of the interferometer 120 of FIG. 1. Referring to FIG. 3, the interferometer 120 of the OCT apparatus, i.e., the tomographic image generating apparatus 100, receives the optical signal OS and splits it into a measurement signal MS and a reference signal RS. To this end, two separate signal paths P1 and P2 are formed in the interferometer 120. The measurement signal MS split from the optical signal OS is transmitted through the signal path P2, and the reference signal RS is transmitted through the signal path P1.

The interferometer 120 may split the optical signal OS into the measurement signal MS and the reference signal RS according to a splitting ratio. The splitting ratio may be defined as a ratio of the output intensity of the reference signal RS to the output intensity of the measurement signal MS. For example, the interferometer 120 may split the optical signal OS into the measurement signal MS and the reference signal RS according to a splitting ratio of 5.5, or a splitting ratio of 9:1, or any other splitting ratio. When splitting the optical signal OS into the measurement signal MS and the reference signal RS using a beam splitter 121 of FIG. 3, the splitting ratio may be determined according to transmission and reflection characteristics of the beam splitter 121.

Referring again to FIG. 1, the interferometer 120 transmits the measurement signal MS to the phase modulator PMD, and a probe 130 applies the measurement signal MS modulated by the phase modulator PMD to the target object 160. The measurement signal MS applied by the probe 130 is reflected or dispersed in the target object 160.

Figure 4:
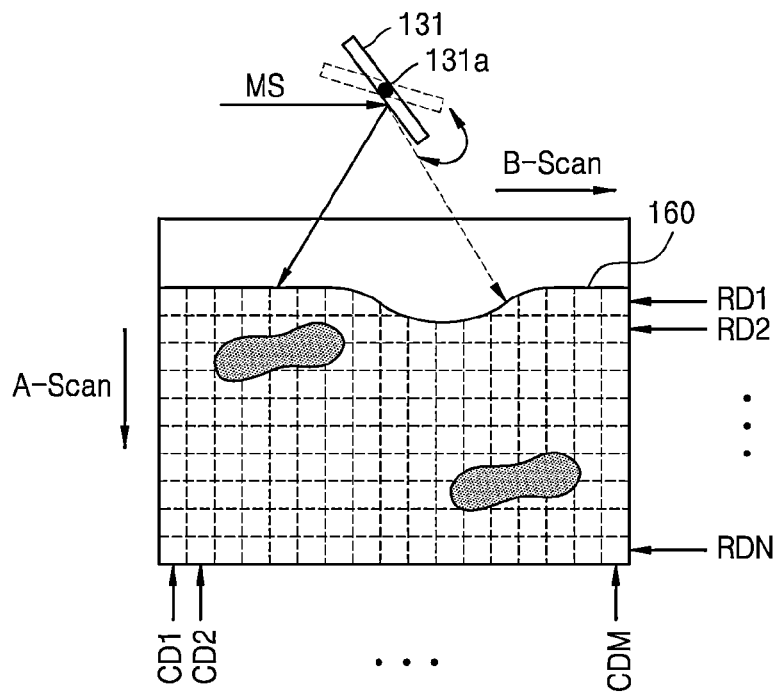
FIG. 4 is a diagram illustrating an example of operation of a phase modulator of FIG. 1.

FIG. 4 is a diagram illustrating an example of operation of the phase modulator PMD of FIG. 1. In FIG. 4, the probe 130 that applies the phase-modulated measurement signal MS to the target object 160 has been omitted for convenience of explanation. Referring to FIGS. 1 and 4, the phase modulator PMD includes a scanning mirror 131. The scanning mirror 131 rotates about an axis 131a that is offset with respect to the measurement signal MS.

As the scanning mirror 131 rotates about the axis 131a, the measurement signal MS is applied in a first direction (i.e., a lateral direction or a row direction) B-Scan of the target object 160 and is phase-modulated due to the offset between the axis 131a and the measurement signal MS. For example, the scanning mirror 131 rotates on the basis of a unit corresponding to one pixel of the row direction of the target object 160 while the measurement signal MS is applied. As a result, the measurement signal MS is phase-modulated on the basis of the unit corresponding to one pixel. The phase modulator PMD may be a galvano scanner, and in this case, the first direction B-Scan corresponds to a direction due to a rotation of the galvano scanner.

The measurement signal MS that is applied to the target object 160 on the basis of a pixel unit of the row direction is reflected or dispersed in a second direction (i.e., a vertical direction or a column direction) A-Scan of the target object 160. In the example of FIG. 4, the second direction A-Scan of the target object 160 is a direction perpendicular to the first direction B-Scan of the target object 160, but is not limited to the perpendicular direction.

The reflected or dispersed measurement signal MS is transmitted to the interferometer 120 as a response signal AS.

For example, the response signal AS may be transmitted to the interferometer 120 through the same path as the path through which the measurement signal MS is applied to the target object 160. Alternatively, the response signal AS may be transmitted to the interferometer 120 through a path that is different from the path through which the measurement signal MS is applied to the target object 160. The response signal AS and the measurement signal MS may be transmitted to and from the interferometer 120 through free space or a transmission medium such as an optical fiber. The interferometer 120 generates the interference signal CS due to interference between the response signal AS and the reference signal RS.

In greater detail, the reference signal RS is transmitted to a reference mirror 122 through the path P1 in the interferometer 120, reflected by the reference mirror 122, and transmitted to the beam splitter 121. A part of the reference signal RS transmitted to the beam splitter 121 is reflected by the beam splitter 121, and the other part thereof passes through the beam splitter 121. The reference signal RS that passes through the beam splitter 121 interferes with the response signal AS reflected by the beam splitter 121 to generate the interference signal CS.

The interference signal CS is transmitted from the beam splitter 121 to the detector 130 and input to the detector 140. The detector 140 detects the interference signal CS, which is generated by the interference between the response signal AS and the reference signal RS, as the raw data RDTA of a frame unit. The raw data RDTA that is formed on the basis of the frame unit may be simultaneously obtained through one rotation operation of the scanning mirror 131 of FIG. 4, or first through M-th columns CD1-CDM of the raw data RDTA may be sequentially obtained through repeated rotation operations of the scanning mirror 131 that correspond to the number of pixels in the first direction.

For example, the detector 140 detects the optical intensity I of the interference signal CS on the basis of a row unit with respect to the target object according to Equation 1 below. In the following equation, "Ir" denotes the optical intensity of the reference signal RS, "Is" denotes the optical intensity of the response signal AS, "k" denotes a wavelength, "Zrs" denotes a path length difference (or a difference of depth information of the target object 160) between the reference signal RS and the response signal AS, "x" denotes the number of pixels in the first direction (i.e., the row direction) of FIG. 4, and "$f_B \cdot x$" denotes a phase-demodulated value.

$$I(k, x) = \sum_{i=0}^{N} 2 \cdot \sqrt{I_r I_{s_i}} \cdot \cos(2k \cdot z_{rs_i} + f_B \cdot x) \quad (1)$$

The detector 140 may detect the optical intensity "I" of the interference signal CS using a light receiving unit (not shown), and examples of the light receiving unit may include a photo detector. A process of detecting an optical interference signal has been described above. However, the tomographic image generating method in this example is not limited to generating a tomographic image from the optical interference signal, and may generate a tomographic image of a target object by detecting other signals indicating information about the tomographic image of the target object and then analyzing the detected signals.

Referring to FIGS. 1 and 2, when operation 220 is performed in the above process, the raw data RDTA detected by the detector 140 is transmitted to the image processing device 200 to generate a tomographic image. The image processing device 200 demodulates the raw data RDTA received from the detector 140 (operation S240), and generates the tomographic image of the target object 160 (operation S260). For convenience of explanation, an electrical signal ES may be used together with the interference signal CS below.

The image processing device 200 includes a fixed window filtering unit 210 and an image generating unit 230. The fixed window filtering unit 210 demodulates the raw data RDTA. The fixed window filtering unit 210 is a filter having a fixed window size, and performs a demodulation operation by adjusting parameters of a filter function defining a filtering operation of the fixed window filtering unit 210, and filtering the raw data RDTA on the basis of a row unit.

Figure 5:
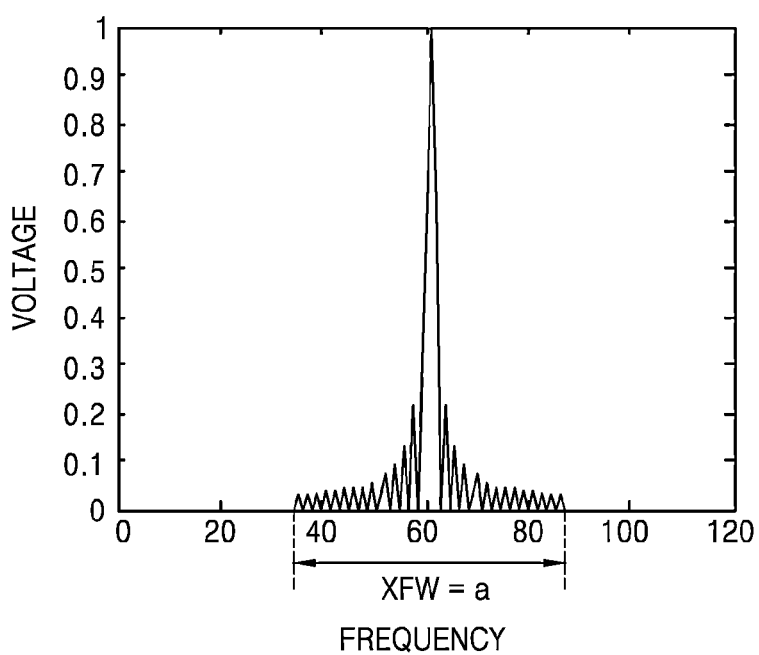
FIG. 5 is a diagram illustrating an example of an operation in which filtering is performed using a fixed window size.

FIG. 5 is a diagram illustrating an example of an operation in which filtering is performed using a fixed window size. Referring to FIG. 5, the fixed window filtering unit 210 may be set with a window having a fixed size corresponding to a window size signal XFW. For example, the fixed window filtering unit 210 may be set with a window having a fixed size "a" (here, "a" is a constant), which is symmetrical about a central value, in response to the window size signal XFW as illustrated in FIG. 5.

In this example, the fixed window filtering unit 210 may be set with the fixed window size before demodulating the raw data RDTA. For example, the fixed window filtering unit 210 may set the fixed window size in response to the window size signal XFW received through the user interface unit 170 when the tomographic image generating apparatus 100 of FIG. 1 is set up or turned on. In this case, the fixed window filtering unit 210 may be set with different window sizes whenever the tomographic image generating apparatus 100 of FIG. 1 is set up or turned on. The window size may be set on the basis of a tap.

As stated above, the filtering operation of the fixed window filtering unit 210 may be defined by a filter function. In this case, in order to filter the raw data RDTA, an operation of multiplying each of rows of the raw data RDTA by a filter function is performed a number of times corresponding to the fixed window size. The filtering operation will be described below with an example of a specific filter function.

Figure 6:
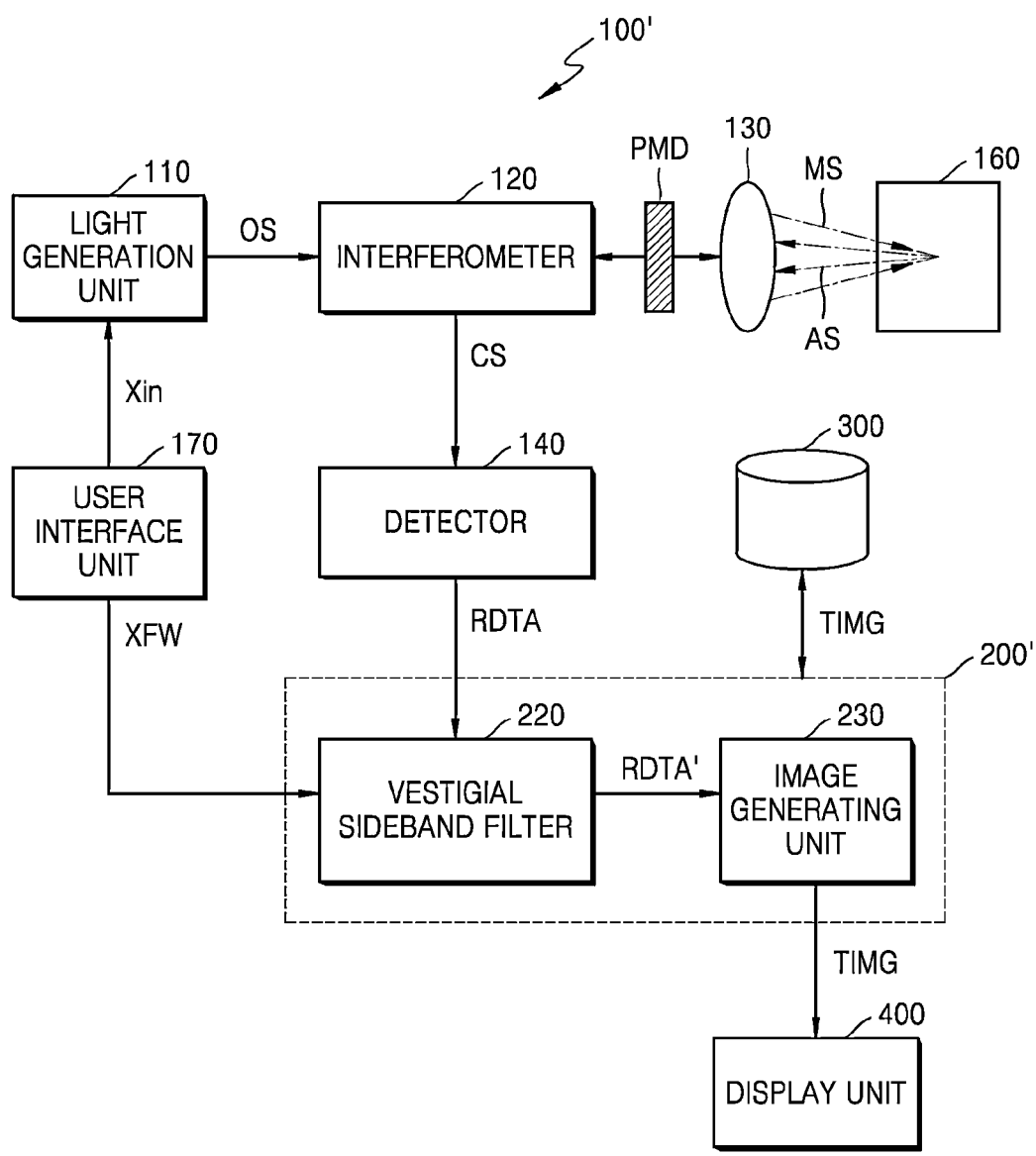
FIG. 6 is a block diagram illustrating an example of an apparatus for generating a tomographic image in which a fixed window filtering unit of FIG. 1 is replaced by a vestigial sideband filter.

FIG. 6 is a block diagram illustrating an example of an apparatus 100' for generating a tomographic image (hereinafter referred to as a "tomographic image generating apparatus") in which the fixed window filtering unit 210 of FIG. 1 is replaced with a vestigial sideband filter (VSB) 220. Referring to FIG. 6, the tomographic image generating apparatus 100' includes an image processing device 200' including the vestigial sideband filter (VSB) 220 and the image generating unit 230. In this case, the filtering operation of the vestigial sideband filter (VSB) 220 may be defined by Equation 2 below. In Equation 2, a function "y" is a demodulation signal that is output as a filtered result signal, and a function "x" is a signal indicating each row of the raw data RDTA. The sum of a function "δ" and a function "h" is a filter function. In addition, "N" denotes a window size.

$$y(n) = (\delta(n) + h(n)) * x(n) \quad (2)$$

$$\approx x(n) + j\frac{2}{\pi}\sum_{k=0}^{N} coeffs(k) \times (x(n - 2k - 1) - x(n + 2k + 1))$$

In Equation 2, it is assumed that the function "h" is expressed by Equation 3 below. Since the value of the function "y" is zero when "n" is an even number, Equation 2 excludes this case.

$$h(n) = \begin{cases} 0 & \text{for even } n \\ \dfrac{2}{n\pi} & \text{for odd } n \end{cases} \quad (3)$$

Accordingly, in the vestigial sideband filter (VSB) 220 of FIG. 6, a multiplication operation is performed with respect to one-half of the window size "N". The coefficient "coeffs" of Equation 2 may be expressed by Equation 4 below. In Equation 4, "T" denotes a duration of the filter function, and "R" denotes a roll-off of the filter function.

$$coeffs(k) = \frac{\sin\left(\frac{\pi k}{T}\right)}{\frac{\pi k}{T}} \cdot \frac{\cos\left(\frac{\pi R k}{T}\right)}{\left(1 - \frac{4R^2 k^2}{T^2}\right)} \cdot e^{\frac{2j\pi k}{4}} \quad (4)$$

As stated above, the tomographic image generating method according to this example may be performed by adjusting at least one parameter of a filter function defining filtering and setting the shape of the waveform of the interference signal with respect to the frequency domain.

Figure 7:
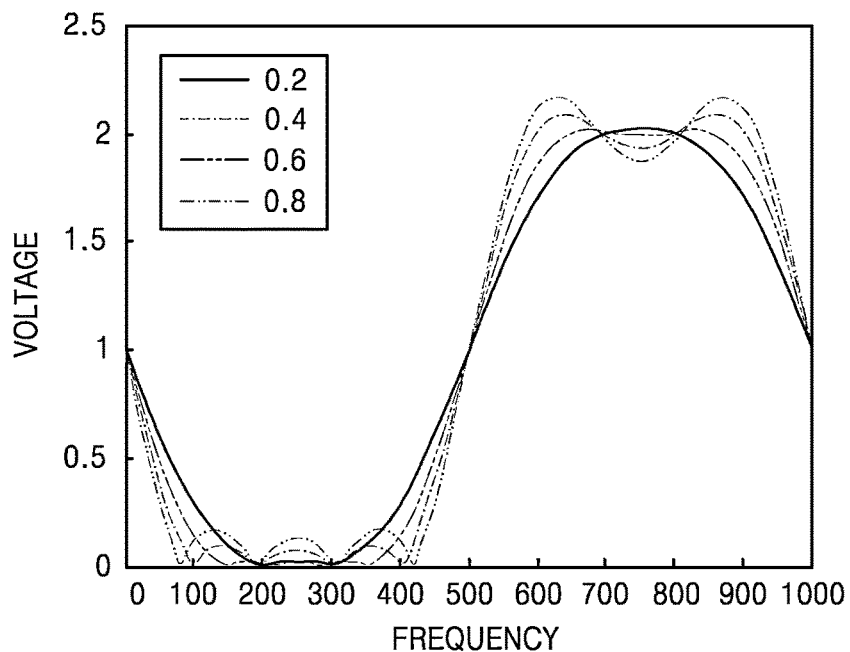
FIGS. 7 and 8 are graphs illustrating examples of a method of demodulating an interference signal by adjusting parameters of a filter function defining filtering.
Figure 8:
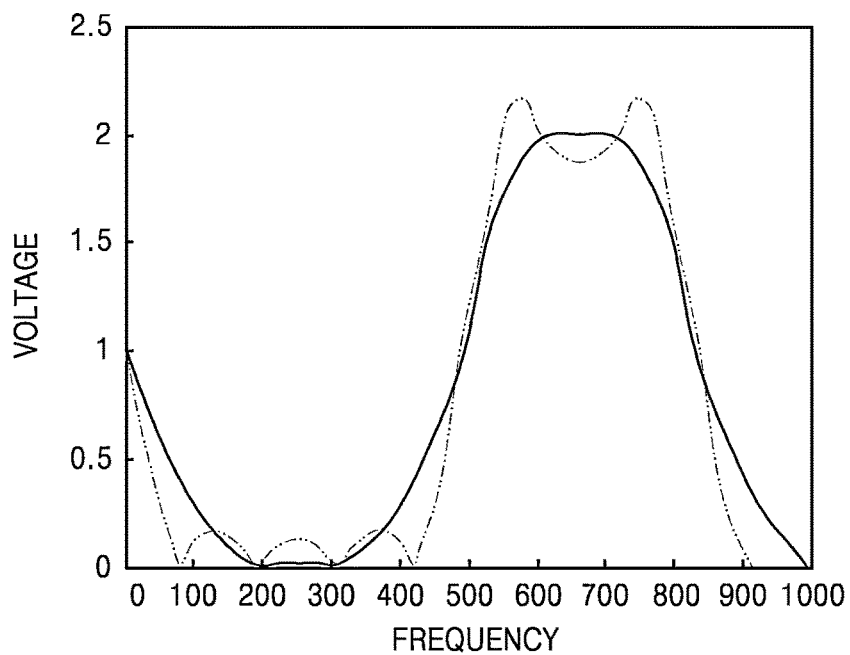

FIGS. 7 and 8 are graphs illustrating examples of a method of demodulating an interference signal by adjusting parameters of a filter function defining filtering.

For example, as illustrated in FIG. 7, when changing a value of the roll-off R of the filter function, a slope of a rising or falling period may be changed in the waveform of the raw data RDTA of the frequency domain. Thus, the flatness of the waveform of the raw data RDTA may be changed. FIG. 7 illustrates an example in which the flatness of the waveform is optimum when the value of the roll-off R is 0.6. However, an optimized value of the roll-off R may change depending on an operational environment, and is not limited to the example of FIG. 7.

In addition, as illustrated in FIG. 8, by changing the duration T of the filter function, the width of the waveform of the interference signal CS of the frequency domain may be changed. In the same manner, the flatness of the waveform of the interference signal CS may be also changed as the width of the waveform of the interference signal CS is changed.

As described above, the tomographic image generating apparatus and method according to this example may improve the flatness of the waveform of a demodulated interference signal by using a fixed window size to perform filtering without changing the number of multiplication operations, i.e., without increasing a complexity of the filtering. Thus, in the tomographic image generating apparatus and method according to this example, the window size, i.e., the number of multiplication operations, does not need to be increased to improve the flatness.

Figure 9:
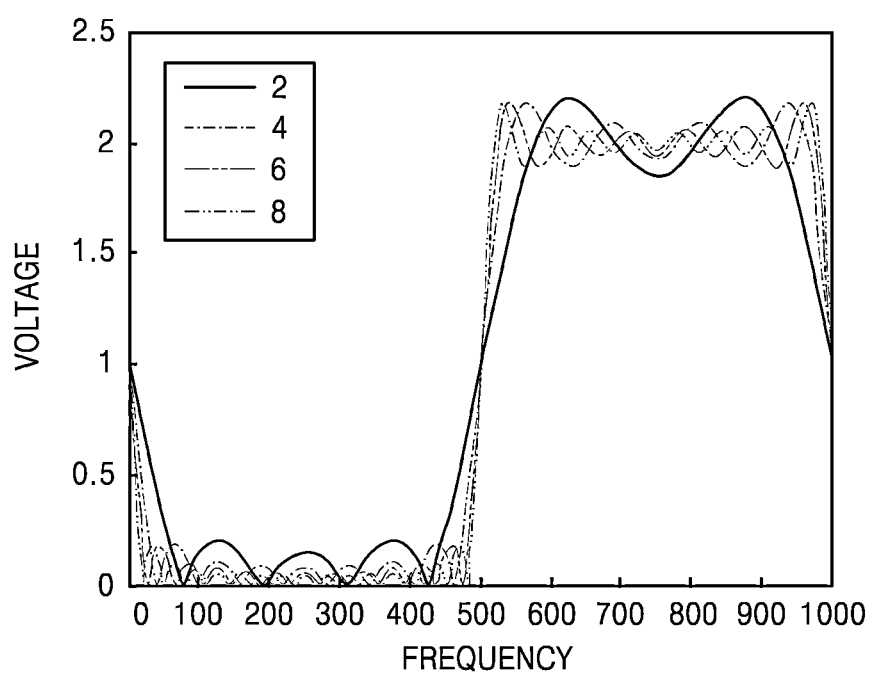
FIG. 9 is a graph illustrating an example in which a complexity of filtering is increased.

FIG. 9 is a graph illustrating an example in which a complexity of filtering is increased. FIG. 9 illustrates the case where the flatness is optimum when the window size is 8, which is the largest, and is worst when the window size is 2, which is the smallest. Accordingly, it is necessary to increase the window size, and thus the number of multiplication operations and the complexity of filtering, to achieve the optimum flatness.

Figure 10A:
FIGS. 10A and 10B are diagrams illustrating examples of a relation between the complexity increase of FIG. 9 and a folding phenomenon.
Figure 10B:
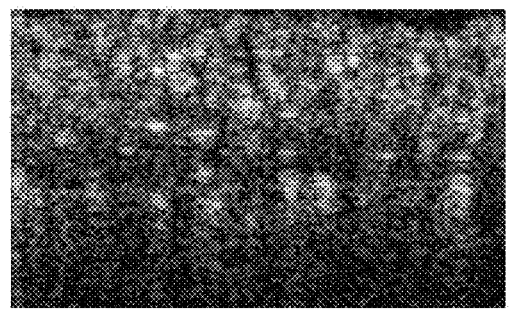

FIGS. 10A and 10B are diagrams illustrating examples of a relation between the complexity increase of FIG. 9 and a folding phenomenon. FIG. 10A shows an example in which four multiplication operations are performed in filtering, and FIG. 10B shows an example in which sixteen multiplication operations are performed in filtering.

When the flatness of the waveform of the demodulated interference signal is poor, a folding phenomenon illustrated in FIG. 10A may occur. However, in order to prevent the folding phenomenon of FIG. 10A, the number of multiplication operations may be increased as shown in FIG. 10B. However, the tomographic image generating apparatus and method according to this example may improve the flatness of the waveform of the demodulated interference signal by adjusting parameters of the filter function as stated above without increasing the number of multiplication operations as shown in FIG. 10B. Thus, the tomographic image generating apparatus and method according to this example may decrease a time necessary for performing a demodulation of the interference signal and consumption of resources, and may also prevent the folding phenomenon.

In addition, as stated above, in generating tomographic images, the tomographic image generating apparatus and method according to this example may maintain a quality of tomographic images and also lower a complexity of a calculation required for demodulation of the raw data by fixing a window size used for filtering when demodulating modulated raw data through the filtering. Furthermore, the tomographic image generating apparatus and method according to this example may further reduce the complexity without bringing about changes between domains such as a time domain and a frequency domain when performing demodulation on the raw data.

Referring back to FIGS. 1, 2, and 6, the image generating unit 230 receives demodulated raw data RDTA' and generates the tomographic image TIMG of the target object 160 by processing the received data (operation 260). For example, when demodulation of the raw data RDTA is performed on the basis of a row unit of the first direction (i.e., the B-Scan direction), signal processing of the image generating unit 230 may be performed on the basis of a column unit of the second direction (i.e., the A-scan direction). The image generating unit 230 may receive the raw data RDTA' demodulated by the fixed window filtering unit 210 on the basis of a row unit (i.e., RD1-RDN of FIG. 4), or all at once. When the image generating unit 230 receives the demodulated raw data RDTA' on the basis of the row unit (i.e., RD1-RDN of FIG. 4), the image generating unit 230 may include a storage unit (not shown) for temporarily storing a demodulation result for each row. When the image generating unit 230 receives the demodulated raw data RDTA' all at once, the fixed window filtering unit 210 may include a storage unit (not shown) for temporarily storing a demodulation result for each row.

The image generating unit 230 performs signal processing by converting the demodulated raw data RDTA' from a wavelength domain to a depth domain. To this end, the image generating unit 230 may perform background subtraction with respect to the modulated raw data RDTA', perform k-linearization, and then perform fast Fourier transformation (FFT), all of which are well know to one of ordinary skill in the art. However, the image generating unit 230 is not limited thereto, and the image generating unit 230 may perform signal processing by converting the demodulated raw data RDTA' from a wavelength domain to a depth domain using any one of various other algorithms known to one of ordinary skill in the art. As a wavelength detected for the target object 160 is processed by using depth information, the image generating unit 230 may generate the tomographic image TIMG of the target object 160.

The generated tomographic image TIMG may be stored in a storage device 300. In addition, the generated tomographic image TIMG may be displayed on the display unit 400. The display unit 400 is a device for receiving an image signal from the image processing device 200 and outputting images, and may be an independent device that is located outside the image processing device 200, or may be a component that is included in the image processing device 200. The image processing device 200 may be implemented by using dedicated chips performing functions of components stated above, and may be implemented by using a general purpose central processing unit (CPU) and a dedicated program stored in a storage unit 300.

The user interface unit 170, the image processing device 200, the fixed window filtering unit 210, the image generating unit 230, the image processing device 200', and the vestigial sideband filter 220 described above that perform the operations illustrated in FIG. 2 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of generating a tomographic image, the method comprising:
   generating an optical signal having a wavelength;
   splitting the optical signal to measure a target object;
   detecting an interference signal including cross-sectional information of the measured target object, as raw data of the target object, the raw data being phase-modulated in a first direction with respect to a cross section of the target object;

demodulating the raw data by adjusting at least one parameter of a filter function defining filtering within a fixed window size to output a demodulated raw data signal; and generating a tomographic image of the target object by performing signal processing on the demodulated raw data signal, wherein the parameters of the filter function include a duration and a roll-off, and wherein the filter function comprises a coefficient defined by a product of
- a sine function of the wavelength and the duration,
- a cosine function of the wavelength, the duration, and the roll-off, and
- a constant derived from the wavelength, the duration, and the roll-off.

2. The method of claim 1, wherein the at least one parameter is a duration or a roll-off of the filter function.

3. The method of claim 1, wherein the demodulating of the raw data comprises adjusting a flatness of a waveform of the raw data by adjusting the at least one parameter.

4. The method of claim 1, wherein the demodulating of the raw data comprises performing an operation of multiplying each of first units of the raw data by the filter function defining the filtering a number of times corresponding to the fixed window size.

5. The method of claim 4, wherein each of the first units is a row unit of the raw data.

6. The method of claim 1, wherein the filter function is a vestigial sideband filter (VSB) filter function.

7. The method of claim 6, further comprising setting a window size of the VSB filter function as the fixed window size before demodulating the raw data.

8. The method of claim 1, wherein the generating of the tomographic image of the target object comprises performing signal processing on the demodulated raw data in a second direction perpendicular to the first direction.

9. The method of claim 1, wherein the demodulated raw data is in a wavelength domain; and
the generating of the tomographic image of the target object comprises converting the demodulated raw data in the wavelength domain into depth information about the target object.

10. The method of claim 1, wherein the method of generating a tomographic image is an optical coherent tomography (OCT) method.

11. A non-transitory computer-readable storage medium storing instructions that, when executed by a processor, cause the processor to perform the method of claim 1.

12. An apparatus for generating a tomographic image, the apparatus comprising:
a light generation unit configured to generate an optical signal having a wavelength;
an interferometer configured to split the optical signal into a measurement signal and a reference signal, and apply the measurement signal to a target object;
a detector configured to detect an interference signal generated by interference between the reference signal and a response signal received from the target object in response to the application of the measurement signal as raw data of the target object, the raw data being phase-modulated in a first direction with respect to a cross section of the target object; and
an image processor configured to demodulate the raw data by filtering the raw data using a fixed window size with a filter function to output a demodulated raw data signal, and
generate a tomographic image of the target object by performing signal processing on the demodulated raw data signal,
wherein the filter function comprises parameters including a duration and a roll-off, and
wherein the filter function comprises a coefficient defined by a product of
- a sine function of the wavelength and the duration,
- a cosine function of the wavelength, the duration, and the roll-off, and
- a constant derived from the wavelength, the duration, and the roll-off.

13. The apparatus of claim 12, wherein the interference signal is in a frequency domain; and
the image processor is further configured to set a shape of a waveform of the interference signal in the frequency domain by adjusting at least one parameter of a filter function defining the filtering.

14. The apparatus of claim 13, wherein the at least one parameter is a duration or a roll-off of a filter function defining the filtering.

15. The apparatus of claim 12, wherein the image processor comprises a vestigial sideband filter (VSB).

16. The apparatus of claim 15, wherein the image processor is further configured to set a window size of the VSB as the fixed window size before demodulating the raw data.

17. The apparatus of claim 12, wherein the image processor is further configured to perform an operation of multiplying the raw data by a filter function defining the filtering a number of times corresponding to the fixed window size.

18. The apparatus of claim 12, wherein the interference signal includes cross-sectional information of the target object as the raw data of the target object; and
the image processor is further configured to demodulate the raw data in first units corresponding to the first direction from the cross-sectional information of the target object.

19. The apparatus of claim 12, wherein the demodulated raw data is in a wavelength domain; and
the image processor is further configured to:
perform the signal processing on the demodulated raw data in a second direction perpendicular to the first direction; and
perform the signal processing by converting the demodulated raw data in the wavelength domain into depth information about the target object.

20. The apparatus of claim 12, wherein the apparatus for generating the tomographic image is an optical coherent tomography (OCT) apparatus.

* * * * *